US011382159B2

(12) United States Patent
Cheaz et al.

(10) Patent No.: US 11,382,159 B2
(45) Date of Patent: Jul. 5, 2022

(54) TEMPORARY EMERGENCY ACCESS TO ARBITRARY NETWORK FOR MEDICAL IMPLANTED DEVICE

(71) Applicant: INTERNATIONAL BUSINESS MACHINES CORPORATION, Armonk, NY (US)

(72) Inventors: Nixon Cheaz, Cary, NC (US); Barton Clark Vashaw, Apex, NC (US); Tomas Znamenacek, Burlington (CA); Jian Zhang, Cary, NC (US); Nanditha Sivashankar, Morrisville, NC (US); Chinh Vien Hoang, Markham (CA); Clayton M. Billups, Cary, NC (US)

(73) Assignee: International Business Machines Corporation, Armonk, NY (US)

(*) Notice: Subject to any disclaimer, the term of this patent is extended or adjusted under 35 U.S.C. 154(b) by 366 days.

(21) Appl. No.: 16/814,329

(22) Filed: Mar. 10, 2020

(65) Prior Publication Data

US 2021/0289576 A1 Sep. 16, 2021

(51) Int. Cl.
*H04L 12/66* (2006.01)
*H04W 76/18* (2018.01)
(Continued)

(52) U.S. Cl.
CPC ........... *H04W 76/18* (2018.02); *A61B 5/0022* (2013.01); *A61B 5/021* (2013.01); *A61B 5/747* (2013.01);
(Continued)

(58) Field of Classification Search
CPC ...... H04L 63/08; H04W 12/06; H04W 76/50; H04W 76/19; H04W 76/18; H04W 76/10; G08B 25/016; A61B 5/747; A61B 5/0022
See application file for complete search history.

(56) References Cited

U.S. PATENT DOCUMENTS 8,782,759 B2 * 7/2014 Hinton .................. H04W 12/06
713/180
8,868,028 B1 10/2014 Kaltsukis
(Continued)

FOREIGN PATENT DOCUMENTS

AU 2018101107 A4 9/2018
CN 106209610 A 12/2016
CN 108924809 A 11/2018

OTHER PUBLICATIONS

Boingo, "Mobile Service Provider", printed Mar. 10, 2020, 11 pages, https://www.boingo.com/.
(Continued)

*Primary Examiner* — Shantell L Heiber
(74) *Attorney, Agent, or Firm* — Teddi E. Maranzano

(57) ABSTRACT

An emergency token for one-time, highly restricted, access to an arbitrary WiFi network, while maintaining full network security and integrity, is disclosed. When an IoT medical device (IMD) detects failure in the IMD, or detects the patient having a medical emergency, IMD detects local active WiFi networks, and attempts connecting to a monitoring center through one of the networks. If the network is password protected, the connection may fail. The IMD retries the connection request using factory-installed one-time use token that is only for emergency calls only. If successful, the IMD sends an emergency message to the monitoring center, which dispatches emergency responder to the location of the IMD. Monitoring center invalidates the token with the central on-line token registrar when both the IMD and the monitoring center acknowledges that the notification is successful. A person having the proper security authorization can install a new one-time use token.

20 Claims, 3 Drawing Sheets

(51) Int. Cl.
    *H04W 4/90* (2018.01)
    *H04L 9/40* (2022.01)
    *A61B 5/00* (2006.01)
    *A61B 5/021* (2006.01)
    *H04W 84/12* (2009.01)
    *G16Y 10/60* (2020.01)
    *G16Y 20/20* (2020.01)

(52) U.S. Cl.
    CPC ............ *H04L 63/0807* (2013.01); *H04W 4/90* (2018.02); *G16Y 10/60* (2020.01); *G16Y 20/20* (2020.01); *H04W 84/12* (2013.01)

(56) References Cited

U.S. PATENT DOCUMENTS

| | | | |
|---|---|---|---|
| 9,179,280 B2 | 11/2015 | Ray et al. | |
| 9,357,370 B2 | 5/2016 | Ray | |
| 10,771,532 B2* | 9/2020 | Polar Seminario | H04L 67/06 |
| 2008/0052399 A1* | 2/2008 | Nguyen | H04M 7/006 |
| | | | 709/227 |
| 2014/0378087 A1* | 12/2014 | Umatt | H04W 4/90 |
| | | | 455/404.1 |
| 2019/0182666 A1* | 6/2019 | Kotay | H04W 12/50 |

OTHER PUBLICATIONS

Diagnostic and Interventional Cardiology—DAIC, "FDA Clears Implantable Heart Attack Warning Device", May 9, 2018, 3 pages.
Wikipedia, "Emergency telephone number", printed Mar. 10, 2020, 10 pages.
Mitchell, "Guest Wi-Fi Network Setup and Tips", Lifewire, Nov. 11, 2019, 6 pages.

* cited by examiner

TEMPORARY EMERGENCY ACCESS TO ARBITRARY NETWORK FOR MEDICAL IMPLANTED DEVICE

The present invention relates in general to data processing systems, in particular, to allowing temporary emergency access to an arbitrary network.

BACKGROUND

Internet of Things (IoT) implanted medical devices (IMD) are increasingly being deployed in patients to improve delivery of patient care. These devices have the potential to reduce healthcare costs by being able to continuously monitor and immediately respond to changes in the patient's metrics. In case of an emergency, either with the patient or with the device itself, the IMD must be able to contact a monitoring center to report the emergency. In some cases the IMD may connect to an open cellular (cell) service, if one is available. Similarly, the IMD may connect to an open WiFi hotspot without a password. However, if the only available WiFi networks that the IMD detects are private and, for security, are password protected, the IMD will not be able to report the emergency to a monitoring center. It is a challenge to preserve the integrity and security of a network, such as an arbitrary WiFi network, balance the patient's safety and yet ensure the ability of the IMD to reach assistance in an emergency. Therefore, it would be advantageous to enable the IMD to have a one-time, temporary, restricted access to a WiFi network on an emergency basis, while maintaining the integrity and security of the network.

SUMMARY

A method, system, and program product are provided for temporary access to a network. In response to an IoT medical device (IMD) detecting a failure, the IMD sends a request for a connection through a router of a network to a monitoring center. Based on the router rejecting the connection request, the IMD retries the connection request, whereby the retried connection request includes a one-time use token. Based on the connection to the monitoring center being successful, the IMD sends an emergency message to the monitoring center. The IMD receives an indication from the monitoring center that an emergency responder is dispatched to a location of the IMD. In response to the IMD acknowledging to the monitoring center receipt of the indication, the monitoring center invalidates the one-time use token.

BRIEF DESCRIPTION OF THE SEVERAL VIEWS OF THE DRAWINGS

In the following, embodiments of the invention are explained in greater detail, by way of example only, making reference to the drawings in which.

DETAILED DESCRIPTION

Figure 1:
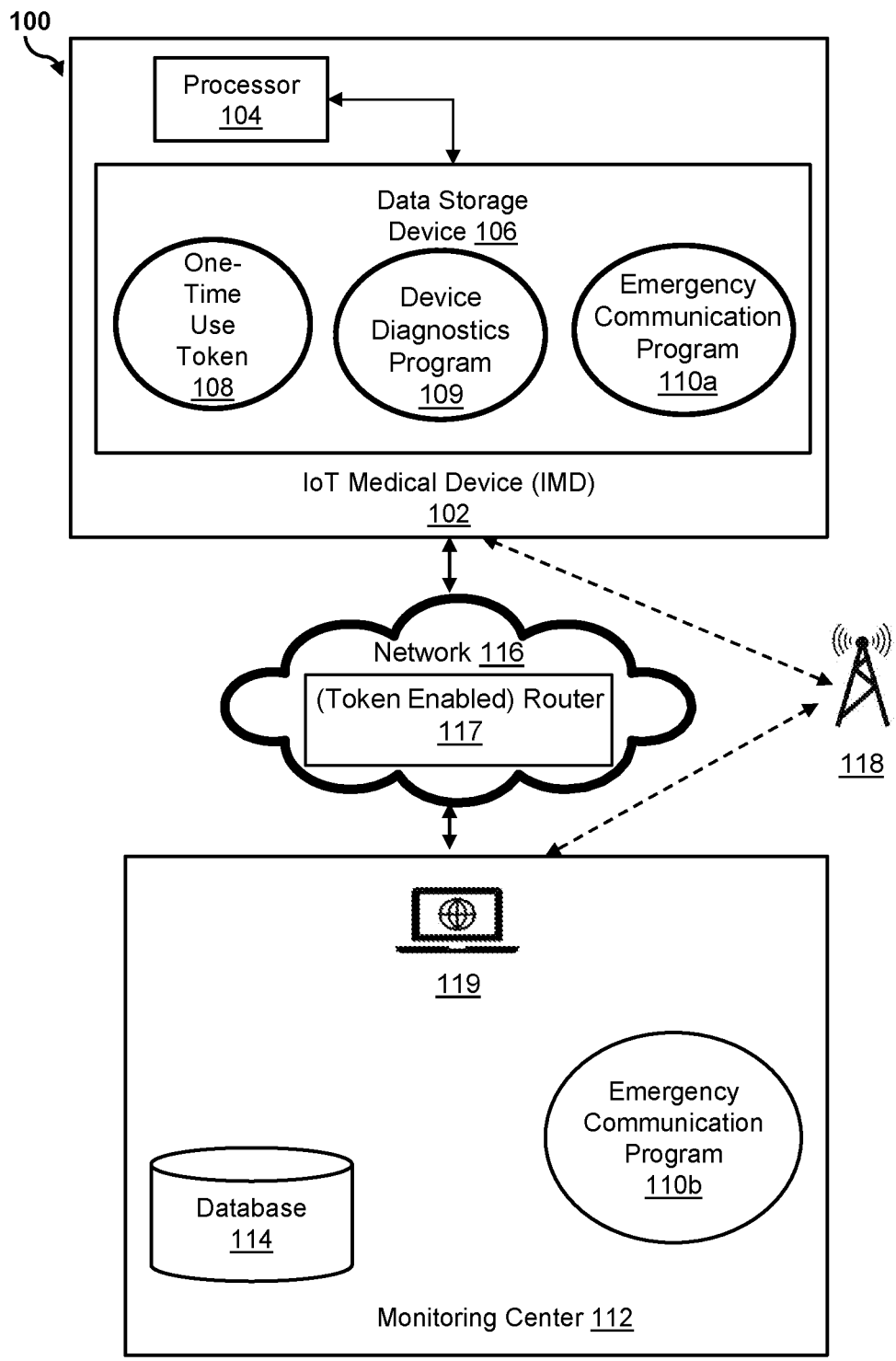
FIG. 1 depicts a schematic of an example of a networked computer environment 100, providing the IoT medical device, according to an embodiment of the present invention.

Internet of Things (IoT) implanted medical devices (IMD) have the potential to reduce healthcare costs by being able to continuously monitor and immediately respond to changes in the patient's metrics. In case of an emergency, either with the patient having an immediate health issue, or with a failure in the device itself, the IMD must be able to contact a monitoring center to report the emergency. The challenge becomes making the connection between the IMD and the monitoring center. In some cases the IMD may connect to an open cellular (cell) service, if one is available. Similarly, the IMD may connect to an open WiFi hotspot without a password. However, if the only available WiFi networks that the IMD detects are private and, for security, are password protected, the IMD will not be able to report the emergency to a monitoring center.

In the drawings, like elements are referred to with equal reference numerals. The drawings are merely schematic representations, not intended to portray specific parameters of the invention. Moreover, the drawings are intended to depict only typical embodiments of the invention and therefore should not be considered as limiting the scope of the invention.

Referring to FIG. 1, an exemplary IoT Implanted Device (IMD) is shown as a networked computer environment 100. The networked computer environment 100 may include the IMD 102 that includes a processor 104 and a data storage device 106. The data storage device 106 stores a one-time use token 108 that the IMD 102 uses to connect to an arbitrary, i.e., any available, WiFi network. The data storage device 106 also stores an IP address by which the emergency communication program 110a can attempt a connection with a monitoring center 112. The data storage device 106 includes device diagnostics program 109 that the IMD 102 periodically executes to determine the health of the device and to determine whether the patient wearing the device experiences an emergency. The data storage device 106 also includes an emergency communication program 110a that the IMD 102 uses to attempt to connect to the monitoring center 112, either directly through a cell service 118, or through an arbitrary WiFi network 116. The emergency communication program 110a also monitors and stores the patient's location, using, for example, the IMD 102 GPS. However, GPS may not be useful or accurate indoors. In that case, the emergency communication program 110a may perform geolocation using the IMD 102 IP address, a hardware embedded serial number, or any similar identifying entity that can be used for the purpose of triangulating and approximating the location of the IMD 102. The frequency of the monitoring and storing of the patient's location may be configurable. When connecting through the network 116, the emergency communication program 110a may send the one-time use token 108 to gain access to the network 116. The network 116 may have has one or more routers between the IMD 102 and the monitoring center 112. The router 117 represents the gateway router to the network 116. If the router 117 allows restricted temporary access, then that router can forward the message through other routers that may exist along the path to the monitoring center 112. As will be described with reference to FIG. 2, the router 117 firmware may or may not be enabled to require a security token from the IMD 102. The networked computer environment 100 also includes the monitoring center 112 that executes the emergency communication program 110b. The emergency communication program 110b receives communications from the emergency communication program 110a on the IMD 102 that either a patient emergency or diagnostic failure is occurring, and in response, sends an acknowledgement to the emergency communication program 110a that help, such as an ambulance, is being dispatched. The connection to the monitoring center 112 may be by an IP address or website URL, shown as 119. Connection by website has the advantage of not being geographically limited, so long as there is cell or WiFi connectivity available.

In other words, the connection is automated by the program and does not rely on a phone connection or human intervention, although representatives may monitor the actions of the IMD 102 and the emergency communication program 110a, 110b for additional security. It should be appreciated that FIG. 1 provides only an illustration of one implementation and does not imply any limitations with regard to the environments in which different embodiments may be implemented. Many modifications to the depicted environments may be made based on design and implementation requirements. For example, although only one monitoring center 112 is shown, there may be multiple monitoring centers 112 available for redundancy. As will be discussed with reference to FIG. 3, the IMD 102 may include internal components 902a and external components 904a, respectively, and the monitoring center 112 may include internal components 902b and external components 904b, respectively.

Figure 2:
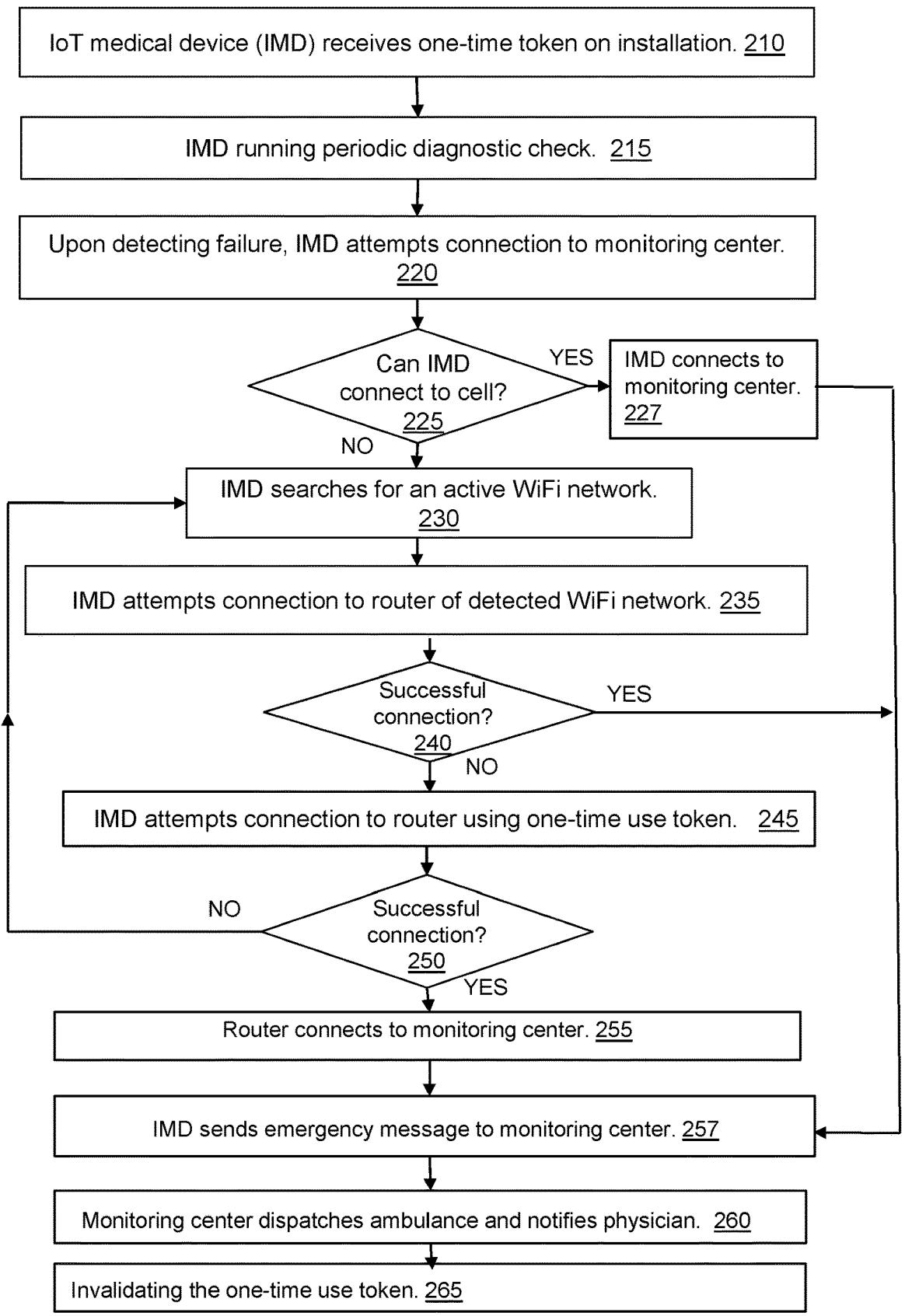
FIG. 2 depicts a flowchart of the IoT medical device having an emergency.

FIG. 2 depicts a flowchart of the IMD 102 attempting to connect to a monitoring center. During the manufacturing process, a one-time use token (token) 108 is installed in the IMD (210). The token 108 may be stored in the data storage device 106.

At 215, the IMD 102 periodically executes a series of diagnostic tests. The frequency of executing the diagnostic tests may be configurable. One set of tests may be provided by the IMD manufacturer to ensure the IMD 102 is operating within the limits of design, for example, testing circuitry and battery level. The physician treating the patient having the IMD 102 may define a separate set of diagnostics to ensure that the patient's metrics are within tolerances. For example, the physician may set tolerances for blood pressure. A range of blood pressures considered normal for the patient may be defined and monitored according to one frequency. Another abnormal range of blood pressures may be defined that trigger increased frequency of monitoring. Finally, if the patient's blood pressure reaches a defined emergency threshold, the IMD 102 initiates an emergency call to a monitoring center. The physician may define similar diagnostics and thresholds for other metrics, such as blood sugar, depending upon the patient and the type of IMD 102. The physician may modify the metric to be monitored and the thresholds, based on changes in the patient's health, such as an improved condition.

At 220, when the IMD 102 detects that one or more of the diagnostic tests failed, the IMD 102 attempts to connect to a monitoring center 112. The failure may be a partial, non-fatal malfunction or failure in the IMD 102, itself, or the patient may be experiencing a health emergency.

At 225, the IMD 102 attempts to connect using a cell service. The cell service may be preferred because it is ubiquitous and does not require proximity to a particular WiFi network for connectivity.

At 227, if the IMD 102 successfully connects to a monitoring center 112 using a cell service, at 257 the IMD 102 sends its emergency message to the monitoring center 112 to which it is connected, where it is received by the emergency communication program 110b. The monitoring center 112 also knows the token 108, and the emergency message can have a digital certificate to establish a circle of trust for the IMD 102. The emergency message includes the patient's location so that the emergency responder can find him with a minimum of searching. The location information may be provided by a GPS on the IMD 102.

The emergency message may include a code associated with the type of failure, and any data included in the emergency message. There may be a separate set of codes from the manufacturer for device related issues, and another set of codes for patient health emergencies. For example, a code may indicate a low battery condition. In response, the emergency communication program 110b may take one of several actions that are defined for the code in the database 114. In response, at 260, the emergency communication program 110b may dispatch an ambulance and notify the patient's physician to what hospital the ambulance is going.

If at 225, the IMD 102 cannot connect to a cell service, at 230 the IMD 102 searches for a nearby active WiFi network.

To ensure the security of their networks, administrators typically require the requestor of the connection to provide identification before receiving authorization and access, such as through including a password. Some administrators of these secure private networks may allow limited, restricted, temporary access to their networks only for emergency purposes through a one-time temporary token 108. During manufacture, the token 108 is installed in the IMD 102. The router 117 has special firmware installed that will allow the IMD 102 limited, restricted, temporary access to that router's network. The router 117 is configured to allow the IMD 102 access only to a restricted list of monitoring centers 112. The emergency message the IMD 102 sends is strictly restricted to a specific format, and no other access is given to any internal or external network that is not part of the emergency communication. The limited access is granted through the IMD being installed with a token 108, and a router 117 having firmware enabled to accept it. The router 117 verifies the authenticity of the token 108 on-line against a registrar that can answer whether the token 108 is both authentic and valid. Both the restricted emergency message format and the restricted list of monitoring centers may be enforced by enhanced validating by the router 117 firmware, as well as by the emergency communication program 110a and 110b. In this way, although the router 117 is granting temporary guest access to its network, the restrictions on the emergency message format and the restricted list of monitoring centers ensures no other access is given to a network not involved with sending the emergency communication.

Having detected an active nearby network, at 235 the IMD 102 attempts to connect to the network's router 117 without using the token 108. A connection between the IMD 102 and the monitoring center 112 may be possible over a WiFi network. This may be the case where the WiFi network is an open or public network that is not password protected, or a private network that is not password protected. If at 240 the connection is successful, then at 127 the emergency communication program 110a sends an emergency message to the monitoring center 112 over the WiFi connection. The emergency message may include a code associated with the type of emergency, a description of the emergency that is associated with the code, and the location of the IMD 102. The emergency communication program 110b at the monitoring center 112 receives the emergency message, and may use some of the information, such as the code, to determine the patient's location, the type of the emergency, and the required response. Based on this determination, the emergency communication program 110b initiates a dispatch of the appropriate emergency responder. The emergency communication program 110b may also send an acknowledgement to the emergency communication program 110a on the IMD 102 and an indication that the emergency responder is on the way.

However, if at 240 the connection is not successful, the emergency communication program 110a attempts to connect to the router 117 of the same WiFi network using the token 108 (245). This is because it is likely that the connection issue is the need for a password to access this network. The connection may not be successful (250) if the router 117 is not enabled due to lacking the required firmware, for example. In this case, the router 117 may simply reject the connection request. In response, the emergency communication program 110a returns to 230 to attempt a connection to the next active WiFi network. The IMD 102 attempts a connection using any active network until a connection is made or the IMD 102 exhausts all the available networks.

At 250, if the emergency communication program 110a successfully connects to the router 117 of the WiFi network, then the router 117 is likely a "one-time use token"-enabled router. At 255, the router 117 completes the connection between the IMD 102 and the monitoring center 112. The router 117 accepts the emergency message from the IMD 102 (257) and forwards it to the monitoring center 112. At 260, the emergency communication program 110b responds in a similar manner to that described above, i.e., determining the assistance required and dispatching the appropriate responder. The patient, however, is not notified unless the patient can connect a device, typically a smartphone, to the internet.

When the IMD 102 receives the notification from the monitoring center 112 that help is dispatched to the location of the IMD 102, the IMD 102 sends to the monitoring center 112 an acknowledgement that the "help is on the way" message is received. Once this exchange is completed, at 265 the monitoring center 112 invalidates the token 108 by pushing an invalidation request for the token 108 to the on-line central registrar of the one-time use tokens.

Once the token is invalidated, a new token must be installed on the IMD 102, however it is not necessary to remove/replace the IMD 102. For example, if the patient is at an emergency facility as a result of the process of FIG. 2, a person who has been properly cleared for security purposes can install a new token. This may be a doctor, personnel from the monitoring center 112, or personnel from the device manufacturer. The doctor is considered an authorized person for this purpose. The authorized person, having the required security role, can authenticate to the IMD 102, since the IMD 102 has a wireless enabled interface. This is to ensure as best as possible that the IMD 102 is not hacked and that the patient's health and security are not compromised. This enhanced authorization is only required for installing the token. To ensure security, the security process can be periodically reviewed and modified as needed. The token is not stored outside of the device because of security concerns that the token may be discovered and used to harm the patient.

Figure 3:
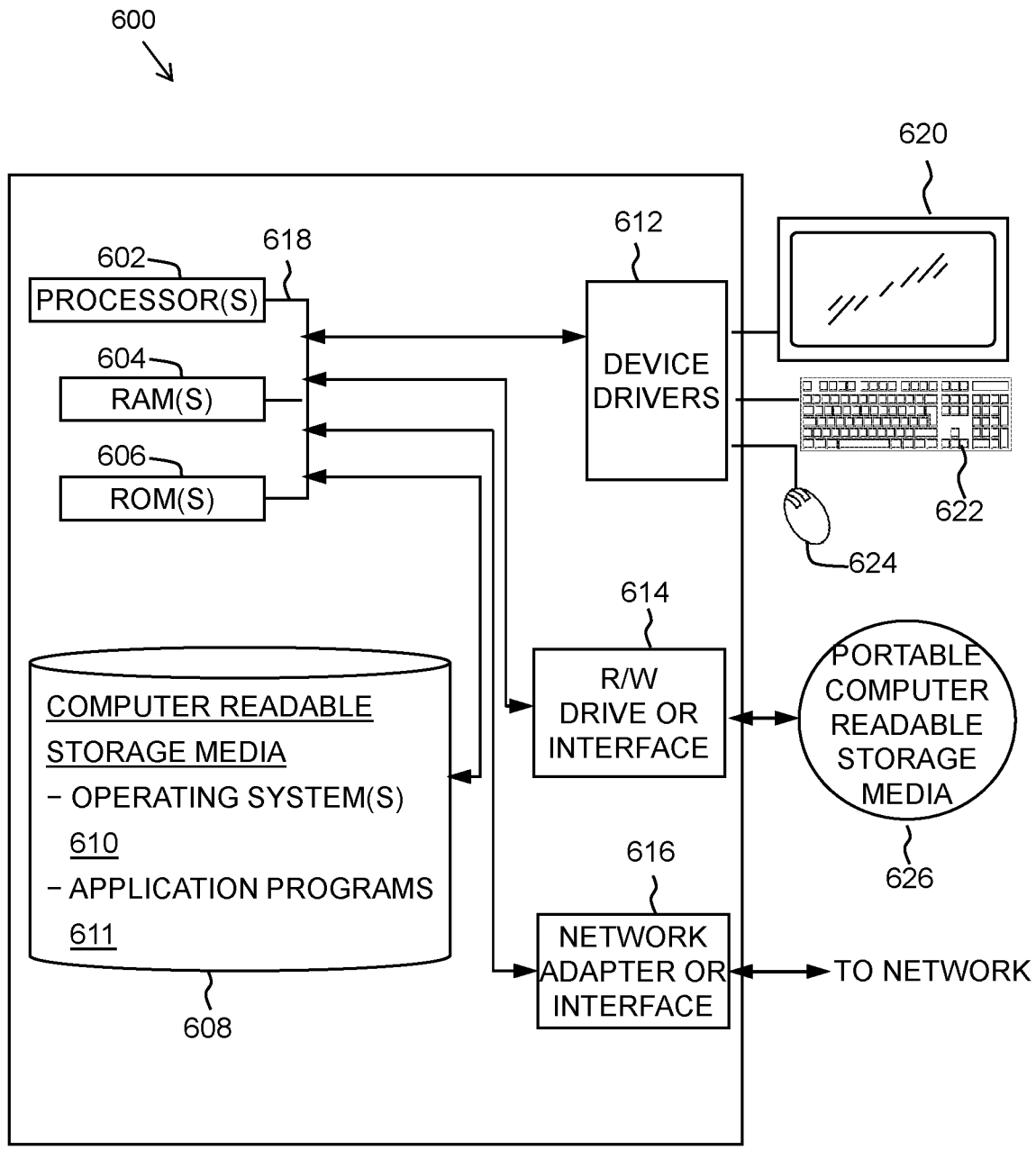
FIG. 3 is a block diagram of an embodiment of a computer system in which the present invention may be implemented.

FIG. 3 depicts a block diagram of components of an example computing device 600 that may provide the form of the IMD 102, in accordance with an embodiment of the present invention. It should be appreciated that FIG. 3 provides only an illustration of one implementation and does not imply any limitations with regard to the environments in which different embodiments may be implemented. Many modifications to the depicted environment may be made.

Computing device 600 can include one or more processors 602, one or more computer-readable RAMs 604, one or more computer-readable ROMs 606, one or more computer readable storage media 608, device drivers 612, read/write drive or interface 614, and network adapter or interface 616, all interconnected over a communications fabric 618. Communications fabric 618 can be implemented with any architecture designed for passing data and/or control information between processors (such as microprocessors, communications and network processors, etc.), system memory, peripheral devices, and any other hardware components within the system.

One or more operating systems 610, and application programs 611, such as the device diagnostics program 109, and emergency communication program 110a are stored on one or more of the computer readable storage media 608 for execution by one or more of the processors 602 via one or more of the respective RAMs 604 (which typically include cache memory). In the illustrated embodiment, each of the computer readable storage media 608 can be a magnetic disk storage device of an internal hard drive, magnetic disk, optical disk, a semiconductor storage device such as RAM, ROM, EPROM, flash memory, or any other computer readable storage media that can store a computer program and digital information, in accordance with embodiments of the invention.

Computing device 600 can also include a R/W drive or interface 614 to read from and write to one or more portable computer readable storage media 626. Application programs 611 on computing device 600 can be stored on one or more of the portable computer readable storage media 626, read via the respective R/W drive or interface 614 and loaded into the respective computer readable storage media 608.

Computing device 600 can also include a network adapter or interface 616, such as a TCP/IP adapter card or wireless communication adapter. Application programs 611 on computing device 600 can be downloaded to the computing device from an external computer or external storage device via a network (for example, the Internet, a local area network or other wide area networks or wireless networks) and network adapter or interface 616. From the network adapter or interface 616, the programs may be loaded into the computer readable storage media 608.

Computing device 600 can be connected to a display screen 620, a keyboard or keypad 622, and a computer mouse or touchpad 624, particularly when the user of the IMD 102 is undergoing a medical procedure performed by a physician needing connectivity to the IMD 102. Device drivers 612 interface to display screen 620 for imaging, to keyboard or keypad 622, to computer mouse or touchpad 624, and/or to display screen 620 for pressure sensing of alphanumeric character entry and user selections. The device drivers 612, R/W drive or interface 614, and network adapter or interface 616 can comprise hardware and software stored in computer readable storage media 608 and/or ROM 606.

The present invention may be a system, a method, and/or a computer program product. The computer program product may include a computer readable storage medium (or media) having computer readable program instructions thereon for causing a processor to carry out aspects of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special-purpose hardware-based systems that perform the specified functions or acts or carry out combinations of special-purpose hardware and computer instructions.

What is claimed is:

1. A method for one-time, restricted, temporary access to a network, comprising:
    in response to an IoT implanted medical device (IMD) detecting a failure, the IMD sending a request for a connection through a router of a network to a monitoring center;
    based on the router rejecting the connection request, the IMD retrying the connection request, wherein the retried connection request includes a one-time use token;
    based on the connection to the monitoring center being successful, sending, by the IMD, an emergency message to the monitoring center;
    receiving, by the IMD, an indication from the monitoring center that an emergency responder is dispatched to a location of the IMD; and in response to the IMD acknowledging to the monitoring center receipt of the indication, the monitoring center invalidating the one-time use token.

2. The method of claim 1, wherein the invalidating the one-time use token further comprises:
after the IMD acknowledges to the monitoring center that the indication is received, the monitoring center pushing a request to an on-line central registrar of one-time use tokens to invalidate the one-time use token.

3. The method of claim 1, wherein detecting the failure further comprises:
periodically executing a series of manufacturer provided diagnostic tests to ensure the IMD is operating within design limits; and
periodically executing a series of physician defined diagnostics to ensure each of a plurality of patient metrics are within tolerances.

4. The method of claim 1, wherein the request for the connection to the monitoring center further comprises:
requesting the connection to the monitoring center using one of a plurality of detected available WiFi networks, wherein the monitoring center is one of a list of plurality of restricted monitoring centers;
based on the one of the plurality of detected available WiFi networks rejecting the requesting connection, sending, by the IMD, the one-time use token and re-trying the connection; and
in response to a successful connection, the IMD sending the emergency message to the monitoring center, wherein the emergency message is restricted to a specific format.

5. The method of claim 1, wherein the IMD connects to the monitoring center using a cell service, a public WiFi network, or a private WiFi network that requires authentication to establish the connection, wherein the one-time use token is the authentication.

6. The method of claim 1, wherein the failure includes a malfunction in the IMD or a patient wearing the IMD having an emergency.

7. The method of claim 1, wherein the emergency message includes: a code associated with a type of failure, data associated with the type of failure, and the location of the IMD.

8. The method of claim 1, wherein the router, the IMD, and the monitoring center each verify that the format of the emergency message, and the restricted list of monitoring centers are enforced, wherein no other access is granted to the IMD.

9. A computer program product for one-time, restricted, temporary access to a network, wherein the computer program product comprises a computer readable storage medium having program instructions embodied therewith, the program instructions executable by a processing unit to cause the processing unit to perform a method comprising:
in response to an IoT implanted medical device (IMD) detecting a failure, the IMD sending a request for a connection through a router of a network to a monitoring center;
based on the router rejecting the connection request, the IMD retrying the connection request, wherein the retried connection request includes a one-time use token;
based on the connection to the monitoring center being successful, sending, by the IMD, an emergency message to the monitoring center;
receiving, by the IMD, an indication from the monitoring center that an emergency responder is dispatched to a location of the IMD; and
in response to the IMD acknowledging to the monitoring center receipt of the indication, the monitoring center invalidating the one-time use token.

10. The computer program product of claim 9, wherein detecting the failure further comprises:
periodically executing a series of manufacturer provided diagnostic tests to ensure the IMD is operating within design limits; and
periodically executing a series of physician defined diagnostics to ensure each of a plurality of patient metrics are within tolerances.

11. The computer program product of claim 9, wherein the request for the connection to the monitoring center further comprises:
requesting the connection to the monitoring center using one of a plurality of detected available WiFi networks, wherein the monitoring center is one of a list of plurality of restricted monitoring centers;
based on the one of the plurality of detected available WiFi networks rejecting the requesting connection, sending, by the IMD, the one-time use token and re-trying the connection; and
in response to a successful connection, the IMD sending the emergency message to the monitoring center, wherein the emergency message is restricted to a specific format.

12. The computer program product of claim 9, wherein the IMD connects to the monitoring center using a cell service, a public WiFi network, or a private WiFi network that requires authentication to establish the connection, wherein the one-time use token is the authentication.

13. The computer program product of claim 9, wherein the failure includes a partial, non-fatal, malfunction in the IMD or a patient wearing the IMD having an emergency.

14. The computer program product of claim 9, wherein the emergency message includes: a code associated with a type of failure, data associated with the type of failure, and the location of the IMD.

15. A computer system for one-time, restricted, temporary access to a network, comprising:
one or more processors; and a computer-readable memory coupled to the one or more processors, the computer-readable memory comprising instructions for:
in response to an IoT implanted medical device (IMD) detecting a failure, the IMD sending a request for a connection through a router of a network to a monitoring center;
based on the router rejecting the connection request, the IMD retrying the connection request, wherein the retried connection request includes a one-time use token;
based on the connection to the monitoring center being successful, sending, by the IMD, an emergency message to the monitoring center;
receiving, by the IMD, an indication from the monitoring center that an emergency responder is dispatched to a location of the IMD; and
in response to the IMD acknowledging to the monitoring center receipt of the indication, the monitoring center invalidating the one-time use token.

16. The computer system of claim 15, wherein detecting the failure further comprises:
   periodically executing a series of manufacturer provided diagnostic tests to ensure the IMD is operating within design limits; and
   periodically executing a series of physician defined diagnostics to ensure each of a plurality of patient metrics are within tolerances.

17. The computer system of claim 15, wherein the invalidating the one-time use token further comprises:
   after the IMD acknowledges to the monitoring center that the indication is received, the monitoring center pushing a request to an on-line central registrar of one-time use tokens to invalidate the one-time use token.

18. The computer system of claim 15, wherein the request the connection to the monitoring center further comprises:
   requesting the connection to the monitoring center using one of a plurality of detected available WiFi networks;
   based on the one of the plurality of detected available WiFi networks rejecting the requesting connection, sending, by the IMD, the one-time use token and re-trying the connection; and
   in response to a successful connection, the IMD sending the emergency message to the monitoring center, wherein the emergency message is restricted to a specific format.

19. The computer system of claim 15, wherein the IMD connects to the monitoring center using a cell service, a private WiFi network that requires authentication to establish the connection, wherein the one-time use token is the authentication, or a public WiFi network.

20. The computer system of claim 15, wherein the emergency message includes: a code associated with a type of failure, data associated with the type of failure, and the location of the IMD.

* * * * *